United States Patent [19]

Archer et al.

[11] 4,439,521
[45] Mar. 27, 1984

[54] METHOD FOR PRODUCING SELF-REPRODUCING MAMMALIAN PANCREATIC ISLET-LIKE STRUCTURES

[75] Inventors: Michael C. Archer, Mississauga; Kanti Jain, Toronto, both of Canada

[73] Assignee: Ontario Cancer Institute, Toronto, Canada

[21] Appl. No.: 313,494

[22] Filed: Oct. 21, 1981

[51] Int. Cl.³ .................... A01N 1/02; C12N 5/00; C12N 5/02
[52] U.S. Cl. .................... 435/1; 435/240; 435/241
[58] Field of Search .................... 435/240–241, 435/1

[56] References Cited

U.S. PATENT DOCUMENTS 4,332,893  6/1982  Rosenberg .................... 435/241

OTHER PUBLICATIONS

Shumakov et al.–Chem. Abst., vol. 91 (1979), p. 155,348x.
Okeda et al.–Chem. Abst., vol. 94 (1981), p. 28,004u.
Dudek R. W. et al., "Morphological Study of Cultured Pancreatic Fetal Islets..." Diabetes, vol. 29, Jan. 1980, pp. 16–21.
Hellerstrom C. et al., "Method for the Large-Scale Isolation of Pancreatic Islets..." Diabetes, vol. 28, Aug. 1979, pp. 769–776.
Nielsen J. W. et al., "Preservation of Beta Cell Function ..." Diabetologia, 16, pp. 97–100 (1979).
Tze W. J. et al., "Long–Term Survival of Adult Rat Islets of Langerhans ...", Diabetes, vol. 26, No. 3, pp. 185–191, Mar. 1979.
Goldman H. et al., "Human Pancreatic Islets in Culture: Effects of ..." Science June, 1976, pp. 1014–1016.
Takaki R. et al., "Long-Term Culture of Isolated Pancreatic Islet Cells", Proc. Soc. for Experimental Biology and Medicine 149, 402–406 (1975).
Hilwig I. et al., "Uber dars Wachstrum de Pankreaszellen von Saugetieren als Monolayer Cultures", Z. Zellforsch 103, 282–290 (1970).

Primary Examiner—Sam Rosen
Attorney, Agent, or Firm—Ridout & Maybee

[57] ABSTRACT

Method for producing pancreatic islet-like structures (ILS's) having histology and insulin-producing properties corresponding to those of fetal pancreatic islets and islets from adult animals maintained in culture. The ILS's are produced by culturing isolated natural pancreatic islets, pancreatic duct pieces, cell clusters consisting of mildly digested pieces of pancreas, cell tissues obtained as by-products of the culturing methods, or previously-produced ILS's, in attachment to a substrate.

50 Claims, 16 Drawing Figures

METHOD FOR PRODUCING SELF-REPRODUCING MAMMALIAN PANCREATIC ISLET-LIKE STRUCTURES

The Government has rights in this invention pursuant to Grant No. 5 RO1 CA26651 awarded by the Department of Health and Human Services.

It is known that isolated pancreatic islets (i.e. islets of Langerhans) and other mammalian pancreatic tissues may be maintained in functional condition producing insulin and other pancreatic hormones for prolonged periods of time in appropriate liquid culture media. These isolated islets can be used for investigations of the normal and abnormal physiology of the mammalian pancreas. The extent to which these investigations can be conducted is, however, limited by the availability of donor animals from which pancreatic tissue can be obtained.

Further, isolated natural islets have in the past been employed in transplantation experiments in which large numbers of isologous islets have been transplanted into animals having chemically-induced diabetes. In these experiments, a lasting amelioration of the diabetic state has been observed. A corresponding approach to human therapy, however, has been hampered by the limited availability of human islet tissue.

The present inventors have developed a method whereby it is possible to produce from mammalian pancreatic tissue functional pancreatic islet-like structures (hereinafter referred to as ILS's) with histological characteristics and insulin-producing properties similar to those exhibited by natural isolated fetal pancreatic islets and by islets obtained from adult animals when maintained in culture. This method may be employed to produce a stock of islet tissue for use in experimental investigations. Large numbers of the ILS's can be produced by the present method from relatively small quantities of pancreatic tissue. Moreover, the ILS's and other cellular materials obtained as a result of carrying out the method may be employed to yield further generations of ILS's (i.e., the ILS's are self-reproducing). The present method therefore provides a means whereby large quantities of experimentally-useful tissue can be produced. Further, in view of the properties of the ILS's, this method may be employable in clinical applications to provide a source of islet tissue for therapeutic islet transplantation.

In the method of the invention, one or more usually a plurality of pancreatic tissue-derived bodies are cultured in a liquid culture medium under conditions promoting mammalian cell growth with the said bodies being attached to a compatible substrate for a period sufficient to result in the neogenesis of ILS's connected to the substrate adjacent the said body or bodies.

The said pancreatic tissue bodies may comprise isolated intact natural mammalian pancreatic islets, small pieces of mammalian pancreatic duct, clusters of coherent pancreatic cells obtained by mild digestion of pieces of whole mammalian pancreas, ILS's obtained from a previously-conducted culturing method, or certain other cell tissues obtained as a by-product of the culturing method. As as described in more detail hereinafter, said isolated islets, pieces of pancreatic duct, and clusters of coherent pancreatic cells, are obtained from postpartal, i.e. neonate, young, or adult, mammalian pancreas.

During the course of the present culturing method, the tissue bodies are attached to or become attached to the substrate in contact with which they are cultured and the ILS's originate from and grow in attachment with cell tissue outgrowing from the original tissue bodies, these outgrowing cell tissues also being in attachment to the substrate. The culturing method is therefore to be carried out in a vessel which provides or contains a substrate which is compatible with mammalian cell tissue and is capable of accepting the attachment of such cell tissue to it. Suitable vessels therefore include tissue culture dishes which, as commercially available, have their bottom surfaces covered with a coating which promotes the attachment of cell tissue thereto. Other culture vessels which provide or contain a suitable substrate surface may of course be employed. In the preferred form, the method is conducted as a stagnant culture i.e. the culture and the liquid culture medium are left in a quiescent state except for changes of the liquid culture medium at intervals. It would, however, be equally possible to conduct the method employing other forms of culturing in which the cells undergoing culture are attached to a substrate immersed in a liquid culture medium.

The culture medium may be any liquid composition capable of sustaining mammalian cell growth. A large range of suitable liquid culture media are available commercially. The cell-growth promoting qualities of any given liquid medium may of course be readily determined by trial and experiment by conducting trial culturings, e.g. with isolated pancreatic islets and determining whether cell multiplication and growth occurs as is evidenced for example by attachment of the islets and subsequent outgrowth of tissue therefrom. One particularly preferred culture medium is alpha tissue culture medium as described by Stanners C. P. et al, "Two types of ribosomes in mouse-hamster hybrid cells", Nature New Biol. 230: 52–54; 1971. It is preferred to add small quantities of glucose to the medium in concentrations corresponding to those occurring in the vivo pancreas e.g. molar concentration of glucose of about 5 to about 20 mM, more preferably about 10 mM, and the culture medium may be equilibrated before use with air containing about 5% $CO_2$ to achieve partial pressures of dissolved gases corresponding to the in vivo condition. Desirably also the medium contains effective concentrations of antibiotics e.g. about 50 to about 200 $\mu$U/ml more preferably about 100 $\mu$U/ml of penicillin and about 50 to about 200 $\mu$g/ml more preferably about 100 $\mu$g/ml streptyomycin to inhibit growth of undesired microorganisms. In the preferred form, the medium also has added to it small quantities of mammalian serum which contains proteins which promote attachment of cell tissues to culture substrates. Preferably the serum is present in an amount of about 5 to 20% by volume, more preferably about 15% by volume, based on the volume of the mixture and is heterologous with respect to the tissue undergoing culture. The effect of any given serum protein in promoting attachment of the pancreatic-tissue derived bodies in the present culturing method can of course be readily determined by trial and experiment. One particularly preferred serum is fetal calf serum. Fetal calf serum contains futin which is known to assist in the attachment of various organisms to culture substrates. A further example is a futin-containing colostrum fraction. Desirably the added serum provides growth factors and proteins which facilitate attachment of the tissue bodies and which are digested by proteolytic enzymes produced by cells in the tissue bodies undergoing culture, thus suppressing any tendency of these cells to self-digestion.

The culture medium is preferably maintained under conditions approximating to the vivo condition which are considered to be adapted to sustain mammalian cell growth i.e. at approximately normal mammalian body temperatures in the range about 35° to 40° C., more preferably at 37° C. and under an atmosphere of a composition e.g. 5%$CO_2$/95% air adapted to maintain the preferred partial gas pressures in solution. Desirably the culture is maintained in a water-saturated atmosphere to avoid undesirable concentration changes in the medium through evaporation losses.

After the initial seeding of the tissue bodies in the culture medium the medium is initially desirably changed at frequent intervals in order to maintain effective nutrient and antibiotic levels in the medium and to wash away any contaminants. For example, for the first 3 or 4 days the medium is preferably changed at intervals of about 12 to 24 hours. Subsequently, it is preferred to change the medium at only relatively long intervals of 5 to 10 days as maintaining the culture for long intervals without medium change inhibits fibroblastic growth.

In the case in which the starting material comprises isolated intact natural pancreatic islets, neogenesis of ILS's has been found to occur when isolated intact natural islets are cultured in attachment to a substrate at low islet population densities, i.e. when a relatively low number of islets are present in the tissue, culture dish or other vessel for the culture medium. In a prior method described in an article by Takaki R. et al "Long-Term Culture of Isolated Pancreatic Islet Cells" Proc. Soc. for Experimental Biology and Medicine 149, 402–406 (1975), neogenesis of ILS's did not occur when the density of islets maintained under culture was 20 islets per ml. Without wishing to be bound by any theory, it is suggested that neogenesis of ILS's is suppressed when there is excessive competition between the islets being cultured. In the present method a density of less than about 10 attached islets per mil of culture medium is employed, more preferably less than about 5 islets per ml of culture medium, still more preferably about 1 to 3 islets per ml.

When carrying out the present method, initially a considerably higher density of islets may be introduced into the culture medium, for example 25 to 40 islets per ml of the medium, as only a small proportion of the islets become permanently attached to the substrate during the culturing and the non-attached islets can be removed from the culture during the course of the culturing procedure so that a culture containing that required low densities of islet population is obtained. The culture of intact isolated islets should typically be maintained for periods of at least about 8 weeks for neogenesis of ILS's to occur. The islets gradually become attached to the substrate during the first four or five days of culture and islets that have remained unattached and free-floating in the medium during that period may be removed from the culture. Typically during the first 5 to 6 weeks of culturing some of the attached islets become detached and may likewise be removed.

It is known from an article entitled "Human Pancreatic Islets in Culture: Effects of Supplementing Medium with Homologous and Heterologous Serum" Goldman, M. et al, Science June 1976, p. 1014 to 1016, that in some instances some islets that become attached to the substrate can rupture and form a monolayer of cells which temporarily attach to the substrate. For reasons which have not as yet been fully elucidated, this rupturing and formation of monolayers has not been observed in the culturing methods investigated by the present inventors. However, as stated in the said article a proportion of the attached islets remain intact while the monolayers break up to form a suspension of cells in the liquid medium, so that in the event that islet rupture occurs the resultant cellular debris can be removed by withdrawal of the liquid medium containing the suspended cells and introducing fresh liquid medium permitting the culture of the remaining intact attached islets to occur.

The isolated islets to be used as a starting material can be obtained by generally known methods for obtaining functional islets from any freshly-obtained mammalian pancreas which is at a sufficiently advanced state of maturity to contain distinct islet bodies i.e. from fetal, neonate or adult animal or human pancreas. The said methods generally comprise comminuting the whole pancreas or a portion thereof and subjecting the comminuted pieces to digestion by shaking them in a solution of an enzyme that lyses connective tissue e.g. collagenase, hyaluronidase, trypsin, and mixtures thereof, for a period sufficient to liberate the islets from the surrounding pancreatic tissue. It is preferred, however, to subject the comminuted pieces to only very mild digestion, e.g. so that the degree of tissue lysis corresponds approximately to that obtained from digestion with a collagenase solution containing about 750 collagenase Units per ml for about 12 to 15 minutes at about 37° C., as it has been found that a smaller yield of ILS's is obtained from pancreatic tissue which has been subjected to harsh digestion conditions. Without wishing to be bound by theory, it is suggested the the neogenesis of ILS's results from the growth of progenitor cells present in the pancreatic exocrine and endocrine ductular elements. In the case of pancreatic islets, it is known that peri-insular and intra-insular ductules are associated with the islets. The tissue of these ductules may contain the ILS-progenitor cells. In the digestion procedure required to liberate the islets, it is therefore preferred to conduct the digestion under such mild conditions that ductular vestiges remain discerable at the peripheries of the isolated islets. It is accordingly preferred to subject the comminuted pancreatic pieces to shaking in contact with the enzyme solution for only the minimum of time required to liberate a substantial number of islets and to use dilute solutions of the enzymes, e.g. with a tissue lysing potency no greater than that of a reference solution containing about 1,500 Units of collagenase per ml, preferably about 1000 Units/ml, more preferably about 750 Units/ml. Moreover, it is preferred to use the relatively milder connective tissue-lysing enzymes collagenase and/or hyaluronidase rather than the more harshly-acting enzyme trypsin which is known to disassociate cells.

In the case in which pieces of pancreatic duct are employed as the starting material, the pieces may be obtained by severing them from the freshly-obtained pancreatic duct of any mammal including humans. As each piece can give rise to a plurality of ILS's it may be desirable to divide the duct into a large number of small pieces in order to increase the yield of ILS's, but it is not essential to comminute the pieces to fine particle size and it is therefore usually convenient to cut the duct manually, using conventional laboratory tools, into pieces of a size which are convenient for handling, and for transfer to the culture vessels. The duct may be cut transversely to yield ring-shaped pieces, or generally flat pieces may be cut from the wall of the duct. Conveniently, pieces of a maximum dimension of from 5 mm to 0.5 mm are employed, more preferably about 2 mm to 0.5 mm. The occurrence of neogenesis of ILS's from the cultured duct pieces is not affected by the population density of duct pieces present in the culture medium, but, as the neogenesis occurs from growth of precursor cells attached to the bottom of the culture dish or other substrate and outgrowing laterally from the duct pieces, it is desirable that a spacing should be maintained between the individual cultured pieces sufficient to avoid overlapping of tissues outgrowing from adjacent pieces, preferably of at least about 5 mm, more preferably at least about 10 mm, so that neogenesis of the ILS's can be observed and harvesting of the ILS's from their points of origin on the substrate adjacent the duct pieces is facilitated.

On seeding the duct pieces into a vessel of liquid culture medium providing a substrate, e.g. the bottom surface of a tissue culture dish, adapted to promote attachment of the duct pieces thereto, usually a proportion of the duct pieces do not become attached to the substrate but remain floating in the medium. Typically, up to about 50% of the pieces do not become attached. Duct pieces which remain unattached after about 2 weeks of culturing may be removed from the culture and may be discarded. Usually also a proportion of the duct pieces that are attached after 2 weeks of culturing subsequently become detached and float in the medium. Typically about 60–70% of the attached pieces subsequently become detached. These detached pieces may likewise be discarded.

A sequence of cell growth leads to the neogenesis of ILS's from the culture of the remaining attached duct pieces. This sequence is the same as that which occurs in the culturing of the attached isolated islets. In each case, the neogenesis of ILS's is preceded by the appearance of a new cell type at the periphery of the body (islet or duct piece). These cells are oblong in shape, highly flattened and are tenaciously attached to the substrate adjacent the body. The flat cells are serrated at both ends and grow in close proximity to one another but do not form continuous sheets. In the case in which isolated islets are used as the starting material, typically the flat cells appear some 8 to 14 weeks, more typically 12 to 14 weeks, after the initial seeding of the islets. In the case of the duct pieces, the time of the appearance of the flat cells varies from duct to duct. Typically the flat cells appear from 2 to 12 weeks, more typically 3 to 12 weeks, after the initial seeding. The flat cells grow only slowly so that for example in the case in which 5 to 10 attached islets are cultured in a 60 mm diameter culture dish, after 3 weeks from their initial appearance in the culture they occupy no more than about half of the area of the dish.

The formation of ILS's commences at the centres of the flat cells during the 3 week period following the first appearance of the flat cells. Initially a small round cell appears which divides quickly to form a multicellular three dimensional structure resting on the large flat cell. The resulting ILS's are spherical, opaque, milky white structures of 50 to 250 $\mu$m diameter. They can be detached by gently streaming liquid culture medium around them and can then be removed from the culture.

During the formation of the ILS's the underlying and neighbouring flat cells begin to disintegrate while new flat cells continue to appear adhered to the substrate at a distance from the newly formed ILS. When these flat cells are cultured, further generations of ILS's are formed, through the sequence of cell growth described above.

Further, ILS's recovered from the culture medium can be re-seeded and produce further generations of ILS's through the sequence of cell growth described above.

The flat cells and the ILS's themselves therefore constitute further classes of tissue bodies which can be cultured to obtain ILS's in the present method.

As mentioned above, a further class of pancreatic tissue bodies which can be employed to generate ILS's by the present method comprises clusters of pancreatic cells obtained by mild digestion of pieces of whole pancreas. The pieces of pancreas may be obtained from human or animal pancreas, by cutting freshly-obtained pancreas into pieces of a size convenient for handling e.g. to 5 to 0.5 mm maximum dimension, more preferably 2 to 0.5 mm maximum dimension and digesting the pieces by shaking them in a solution of a connective tissue-lysing enzymes. It has been found that mild digestion conditions are preferable, as this gives rise to an increased yield of ILS's in subsequent culturing of the tissue. Thus it is preferred to use mild digestion conditions the same as or similar to the digestion procedures described above for liberating intact islets from pancreas pieces.

On seeding these mildly-digested clusters in a tissue culture vessel providing a substrate, e.g. the bottom surface of the culture dish, adapted to promote attachment of cells thereto, typically about 50% of the digested clusters become attached to the substitute within 48 hours. The unattached clusters may be removed to other suitable culture vessels where they become attached within the next 48 hours. The attached clusters spread out to form epitheloid attached granulated cell monolayers and in order to facilitate subsequent harvesting of ILS's it is therefore desirable to arrange the clusters initially at a spacing which avoids overlapping of the resulting monolayers. During the culturing the epitheloid cells are gradually replaced by a second type of epitheloid cell having no visible granules and these become surrounded and covered by a layer of fibroblast cells. The ILS's are formed and grow in attachment to this stromatic layer after a period of culturing of from about 25 to 28 days from the time of the initial seeding, and are morphologically similar to the ILS's obtained from the isolated islets and the duct pieces described above. They can be detached and harvested by gently streaming liquid culture medium around them.

Although the method for producing ILS's in accordance with the invention has been described above in sufficient detail to permit one skilled in the art to carry out the method, for the avoidance of doubt some detailed examples of the method will be given with reference to the accompanying micrograph drawings in which FIGS. 1 to 12 relate to the culturing of rat tissues and FIGS. 13 to 16 relate to culturing of human neonate tissues. More particularly.

PRODUCTION OF ILS'S FROM ISOLATED INTACT ISLETS

Pancreata from freshly sacrificed fed rats (6 to 7 weeks old) are excised and then distended by injecting Hanks balanced salt solution into interstitial spaces at multiple foci through a 25 gauge needle. The organs are trimmed of fat and finely minced with scissors. The pancreatic pieces are then transferred to a 10 ml round-bottom screw cap vial which serves as a digestion flask. Hanks solution containing collagenese (5 mg/ml, 149 units per mg), hyaluronidase (0.75 mg/ml) and 4.5 mM glucose is added to give a final volume of 4 ml. Islets are liberated after 12-15 minutes incubation at 37° with vigorous shaking. The digest is washed repeatedly at room temperature and islets are harvested individually with the aid of a Pederson constriction micropipet, and transferred to Hanks solution containing 1 mg/ml bovine serum albumin. All procedures are performed aseptically.

200 to 250 islets are transferred to a 60 mm diameter X 15 mm tissue culture dish (Falcon Plastics, Oxnard, California) containing alpha tissue culture medium (obtained from the media department Ontario Cancer Institute, Toronto, Canada) enriched with 10 mM glucose and 15% heat inactivated fetal bovine serum obtained from Flor Laboratories, McLean, Virginia, U.S.A. The medium is previously equilibrated at 37° with 5% $CO_2$ in air. After 3 washes, islets are seeded in dishes containing 4 ml of the same medium. The dishes are maintained at 37° C. under a water saturated atmosphere of 5% $CO_2$/95% air. Medium is changed every 24 hrs for 3 days and then twice weekly for 3 weeks. Thereafter, medium changes are made every 7-10 days until the appearance of flat cells (described below).

Initially, 100-150 islets are seeded in 4 ml of tissue culture medium. At the beginning of the culture period (24-72 hr) most of the islets remain unattached to the bottoms of culture dishes. Thereafter, islets gradually become attached (4-5 days). Some islets, however, do not become attached and are removed from the dishes when the medium is changed on the 10th day. Although a few fibroblastoid cells appear at the peripheries of the attached islets, there is no extensive overgrowth of such cells even after 3 weeks. After two weeks in culture, the medium is changed only once in 7-10 days. With this schedule, fibroblastic spread is inhibited almost completely, and the remaining islets become slightly flattened at their margins. With each medium change, during the first 5-6 weeks, a few islets (mostly larger and medium sized) become detached and rounded. These are removed with each change of medium, so that by the end of 10 weeks, each dish contains only a few (5-10) islets of the smallest size.

Figure 1:
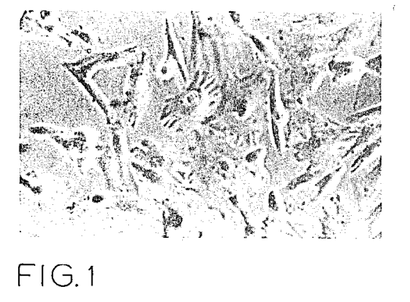
FIG. 1 shows an area of a culture including a flat cell derived from a cultured islet with a round cell (precursor of an ILS) on the upper surface of the flat cell (X 140)
Figure 2:
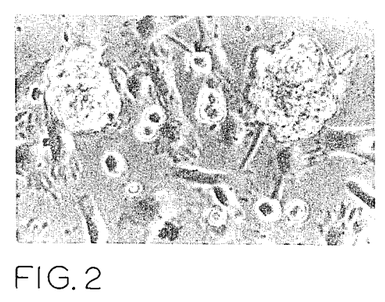
FIG. 2 shows formation of ILS's resting on flat cells (X 140)
Figure 3:
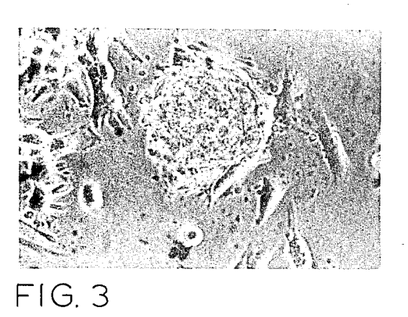
FIG. 3 shows further growth of ILS's (X 140)
Figure 4:
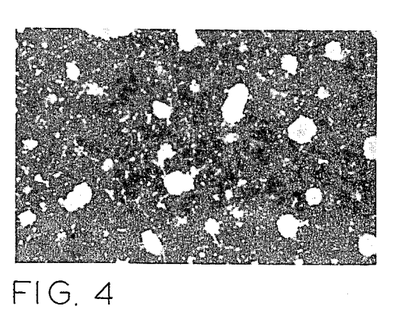
FIG. 4 shows ILS's under phase contract microscopy (X 30)
Figure 5:
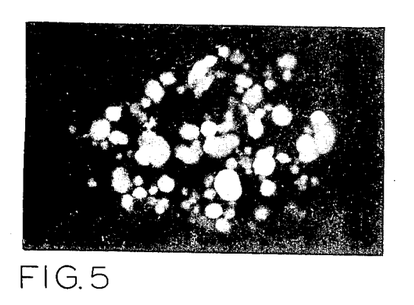
FIG. 5 shows ILS's under dissecting microscopy (X 30)

After 12-weeks under phase contrast microscopy a new cell type is visible at the peripheries of the individual islets. These cells are characterized by being oblong in shape, highly flattened and being tenaciously attached to the culture dishes. These flat cells are shown in FIG. 1. They are highly serrated at both ends. Although these flat cells grow in close proximity to one another, they do not form continuous sheets. They grow very slowly, so that even 3 weeks after their first appearance, they occupy just half the area of the 60 mm dish. During this 3 week period, a number of unique structures form throughout the dish. A few small round cells which are precursors of ILS's first appear at the centres of some of the large flat cells described above, as shown in FIG. 1. These new round cells divide quickly, each forming a multicellular, three dimensional structure (an ILS) resting on a bed provided by the large flat cell as shown in FIG. 2. Under the dissecting stereomicroscope the gross morphology consists of spherical, opaque, milky white structures, 50-250 μm in diameter, similar to freshly isolated pancreatic islets of Langerhans as shown in FIG. 5. During the formation of these ILS's the underlying and neighbouring flat cells begin to disintegrate as shown in FIG. 3 while new flat cells continue to appear at a distance from the newly formed ILS. At completion, this process results in formation of an ILS encompassed by an acellular halo, which in turn is surrounded by increasing numbers of flat cells. These peripheral flat cells can serve as initiating sites for further generations of ILS's.

As noted above, ILS's can be produced from different kinds of tissue. When medium change is performed, the original medium is found to contain a number of free-floating cells. Instead of discarding this medium, these cells may be continued to be maintained. This results in a proliferation of the flat cells and again the formation of ILS's.

Figure 6:
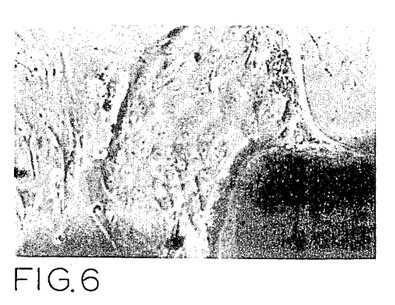
FIG. 6 shows a duct piece under culture giving rise to adjacent cell growths of two types (X 70)

When individual petri plates have accumulated large numbers (400-600) of ILS's as shown in FIG. 6, a few of the older and larger structures appear to become fragile and finally they disintegrate. These disintegrate ILS's are removed during medium change. The remaining healthy ILS's can be easily mobilized by the gentle streaming of culture medium around them. This facilitates the harvesting of the ILS's for use or for continued culture. The subcultured ILS's behave identically to freshly isolated islets in their ability to initiate a new cycle of ILS formation. When one continues to incubate dishes from which ILS's had been harvested, the remaining flat cells also have the potential to form a new generation of ILS's.

PRODUCTION OF ILS'S FROM PANCREATIC DUCT PIECES

The main pancreatic ducts obtained from freshly sacrificed fed rats (6 to 7 weeks old) are freed of surrounding acinar and connective tissue, and are aseptically transferred to a culture dish containing alpha tissue culture medium. The ducts are cut transversely into small (1 mm) pieces, washed 3 times in culture medium, and seeded in 60×15 mm tissue culture (Falcon Plastics) containing 3 ml of alpha tissue culture medium. Each rat provides enough duct for 7-10 dishes, each containing 3-4 pieces. The medium is changed every 2-3 days.

The pieces attach to the bottoms of the dishes with a frequency of about 50%. After one week, examination by phase contrast microscopy reveals a complete absence of acinar and islet tissue. Occasionally, small ductules are observed attaching to the larger pieces. Two patterns of cell growth originate from these attached duct pieces. In a few dishes, only one pattern is observed, while in the others, both are evident.

The more frequency patterns, observed for 60-70% of the attached duct pieces, begins 2 weeks after seeding. Sheets of small polygonal, closely packed cells appear at the peripheries of some of the duct pieces as shown in FIG. 6, in which the dark areas at bottom left and bottom right are duct pieces. The area extending from top to bottom in the middle is a monolayer of the said small polygonal cells. To the left, flat cells with serrated ends appear. The said monolayers of polygonal cells are completely devoid of any fibroblastic growth. After a short time (7-10 days), these cells begin to disappear. Meanwhile, in some instances the duct pieces become rounded off, detach from the bottoms of the dishes and float in the medium. On further incubation of these floating pieces, or their transfer to a new dish containing either fresh or conditioned medium they do not become attached again and they can be discarded.

Figure 7:
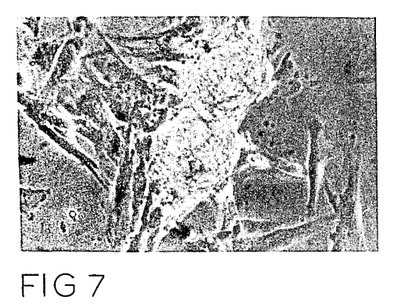
FIG. 7 shows two ILS's derived from duct pieces

The less common pattern of cell growth originating from attached duct pieces is the formation of ILS's as shown in FIG. 7 in a manner identical to the sequence observed when using isolated pancreatic islets as starting material (FIGS. 1 to 5). The time of appearance of the flat cells is unpredictable, varying from duct to duct. In a few instances they appear within 3-4 weeks of seeding the explants. On other occasions, flat cells are observed only after 10-12 weeks. As before, ILS's forming on the flat cells may be mobilized by gently streaming culture medium around them and may be removed from the culture dish for use or for continued culture. In some dishes fibroblastic cells appear along with flat cells. These culture dishes may be discarded.

In general, ILS's derived from both duct pieces and islets are spherical or ovoid in shape, comparable to freshly isolated rat pancreatic islets. Some, however, show an irregular appearance. ILS's derived from pancreatic duct tend to be more variable in shape. Some ILS's have finger-like projections. The majority of ILS's present a very distinct border between central and peripheral portions. Although most ILS's grow as single entities, their appearance in groups is not uncommon. In a number of instances, several ILS's are observed to be enclosed together in loose strands of tissue.

Figure 8:
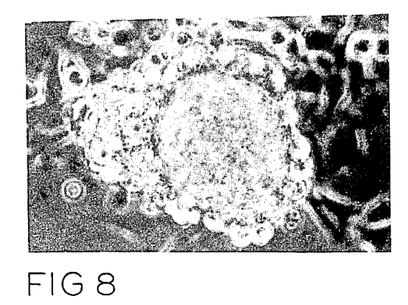
FIG. 8 shows an ILS derived from a duct piece (X 190)
Figure 9:
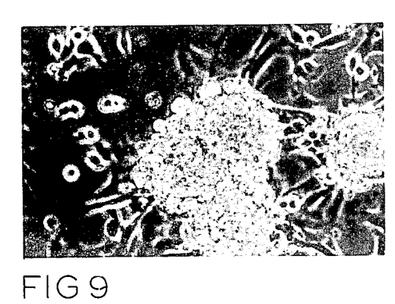
FIG. 9 shows three ILS's in close proximity and a single ILS to the right (X 70)

In some cases, the ILS's derived from duct pieces exhibit a somewhat looser appearance than usual, and there may be repeated cellular outbuddings from the periphery as shown in FIG. 8. These cells are variable in size, and when replated they spread and then form new ILS's as described above and as shown in FIGS. 8 and 9.

In each case, in the culturing of both isolated islets and duct pieces, one month after their first appearance, large numbers of ILS's accumulate in the original culture dishes. At this time the ILS's may be subcultured by transferring a few of them to a new dish containing fresh medium. This process of multiplication continues and necessitates subculturing at 3-4 week intervals.

HISTOLOGICAL CHARACTERIZATION

Figure 10:
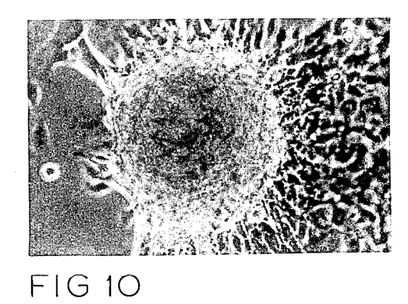
FIG. 10 shows an older ILS (X 80)
Figure 11:
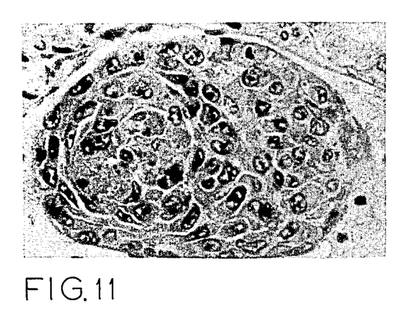
FIG. 11 shows a section of a young ILS stained with haemotoxylin-eosin (X 180)
Figure 12:
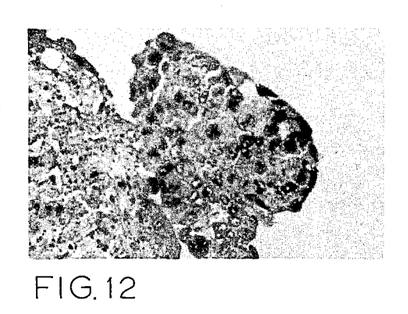
FIG. 12 shows a younger ILS (on the right) budding from an older ILS (on the left)

Histological studies indicated that the majority of ILS's are oval in shape and consist of polyhedral cells. Cytoplasm is found to be eosinophilic with routine haematoxylin and eosin stain. Nuclei are round or oval, and in general are of uniform size. In the smallest islets, all cells are found to be well preserved (FIG. 11); however, central necrosis is observed to varying degrees in medium and larger ILS's (FIGS. 10 and 12). The peripheral cells and the cells of new buds, however, always remain well preserved (FIG. 12).

INSULIN CONTENT OF ILS'S

Insulin content of ILS's was determined by sonicating groups of 100 ILS's in 1 ml of acid alcohol (67 ml ethanol, 31 ml water, 2 ml 12 N HCl) and extracting them for 24 hr. at 4° C. After centrifugation (30,000 xg, 30 min., 4° C.), the supernatants were decanted, dried under a stream of nitrogen, and finally reconstituted with assay buffer. Insulin was determined by the radioimmunoassay technique described by Hales and Randle "Immunoassay of insulin with insulin antibody precipitate" Biochem. J. 88: 137-146 (1963) using an assay kit obtained from Amersham, Oakville, Canada, in which human insulin was provided as a standard.

Insulin content for all generations of ILS's derived from both pancreatic duct pieces and isolated islets, was a constant 90-120$\mu$ Units/ILS. The medium in which the ILS's is cultured accumulates a fairly large amount of insulin (500-900$\mu$ Units/ml) during a 48 hr period. Because large numbers of ILS's disintegrated, it is not possible to determine how much of the hormone is attributable to active secretion or cellular deterioration.

BIOSYNTHESIS OF PROINSULIN-INSULIN AND OTHER PROTEINS OF ISLET-LIKE STRUCTURES

Protein biosynthesis was determined by measuring the incorporation of [3H]-leucine into immunologically reactive proinsulin-insulin as well as trichloroacetic acid preciptable proteins. ILS's was washed 3-4 times in Krebs Ringer bicarbonate buffer (KRB) and transferred individually to glass tubes. Each tube received 15-20 ILS's. ILS's were first preincubated in 300 $\mu$l of buffer containing 4 mM glucose and 1 mg/ml albumin. Incubation was carried out at 37° C. in a Dubnoff metabolic shaking incubator under an atmosphere of 95% $O_2$/5% $CO_2$. After 45 minutes the buffer was replaced by 300 $\mu$l of fresh buffer containing 20 mM glucose and 100 $\mu$Ci/ml of L-[4,5-3H]-leucine (40 Ci/mmole). After a further 90 min. incubation, buffer was removed and the ILS's were washed 3 times with ice-cold KRB containing 3 mM leucine. The islets were sonicated in 100 $\mu$l of acid alcohol and then extracted in 1 ml of acid alcohol for 24 hr at 4° C. The islet sonicate was then centrifuged (30,000 g. 30 min., 4° C.) and a 100 $\mu$l aliquot of the extract was used for the determination of radioactive proinsulin and insulin by the double antibody precipitation method described by Zucker and Logothetopoulos. Diabetes. 26: 194-200 (1975).

Biosynethesis of proteins not extracted by acid alcohol was determined by measuring [3H]-leucine incorporation into trichloroacetic acid precipitable protein. Sonicated, acid alcohol extracted islet pellet was dissolved in 0.3 ml of 0.5 N NaOH for 20 min at 37° C. Four ml of ice cold TCA (12%) containing 3 mM leucine were added. After 2 hr at 4° C. the precipitate was trapped on a Whatman GF/A glass microfibre filter and washed 3-4 times with 6% TCA containing 3 mM leucine. Filters were transferred to glass scintillation vials and the precipitate solubilized in 0.5 ml formic acid. Ten ml of Aquasol were added and radioactivity determined in a Nuclear Chicago liquid scintillation counter. Incorporation of [3H]-leucine into acid alcohol extractable protein was determined in a similar manner by transferring 100 μl of acid alcohol extract directly into TCA.

The rates of [3H]-leucine incorporation into proinsulin-insulin and total protein at 20 mM glucose are given in Table 1. About ⅓ to ½ of the counts incorporated into TCA precipitable protein from acid alcohol extracts were immunoprecipitable. Most of the newly synthesized protein was, however, not extracted with acid alcohol, so that, as with natural fetal islets, newly synthesized hormone accounts for only 6-11% of total protein synthesized.

TABLE 1

Protein Biosynthesis ([$^3$H]—Leucine Incorporation) by Culture Derived ILS's

| | cpm/2 hrs/ILS | | | Biosynthesis of |
|---|---|---|---|---|
| | Acid Alcohol Extractable Proteins | | TCA Precipitable Proteins | Proinsulin + Insulin |
| Isolate | Proinsulin + Insulin | TCA Precipitable Proteins | not extracted by Acid Alcohol | as % of Total Protein |
| 1 | 5,910 | 17,216 | 65,746 | 7.1 |
| 2 | 13,385 | 25,886 | 98,083 | 10.8 |
| 3 | 5,959 | 16,596 | 81,753 | 6.1 |

Note:
Biosynthesis was estimated in the presence of 20 mM glucose by measuring the incorporation of [3H—leucine] into both proinsulin + insulin and trichloracetic acid precipitable proteins, as described above. ILS's derived originally from pancreatic duct, were selected from 3 different isolates.

INSULIN RELEASE

Groups of 20 ILS's were transferred to glass tubes and incubated in 200 μl KRB containing 5 mg/ml bovine serum albumin, and either 4 or 20 mM glucose. Some tubes also contained 10 mM caffeine or 10 mM theophylline. Incubation was performed for 60 min. in a Dubnoff metabolic shaking incubator as described above. At the conclusion of the incubation period, incubates were frozen for later determination of insulin content. The ILS's were sonicated and remaining insulin was extracted in acid alcohol. Insulin content was determined by radioimmunoassay as described above.

During short term incubations in KRB, insulin release occurred at a rate of 3-5μ Units per ILS per 90 min. Unlike the typical situation with freshly isolated islets, hormone release from these ILS's was unresponsive to high glucose, even in the presence of theophylline or caffeine. This behaviour is similar to that of natural fetal islets and of islets obtained from adult animals that have been maintained in culture.

PRODUCTION OF ILS'S FROM CELL CLUSTERS

The tissue obtained from a non-viable female human neonate bearing an encephalocele is used. As soon as possible after delivery (which was mechanically induced at term), a portion of the pancreas is immediately resected aseptically, and transported to the laboratory in ice-cold alpha tissue culture medium, containing 10 mM glucose, 100 μU/ml penicillin and 100 μg/ml streptomycin. The gland is trimmed free of fat and minced into 1 mm pieces. The pieces are washed several times with medium, then rinsed 3 times in Hanks balanced salt solution at room temperature. About 1 ml of tissue is transferred to each of five 10 ml round bottom screw cap tubes, which serve as digestion vials. Each tube receives 3 ml of enzyme mixture in buffer containing 4.5 mM glucose. In 3 tubes the enzyme mixture consists of 5 mg/ml collagenase (Worthington Biochemical Co., Freehold, N.J., 149 Units per mg) supplemented with 0.75 mg/ml hyaluronidase (Sigma Chemical Co., St. Louis, Mo.) in Hank's buffer. In the remaining tubes 0.25% trypsin solution (Grand Island Biological Co., Grand Island, N.Y.) is supplemented with 1 mg/ml collagenase. Digestion is achieved by hand-shaking the vials for 12-15 min. at 37° C. The tissue digests are washed 7 times with Hanks solution, 3 times with medium containing 15% heat inactivated fetal calf serum, and finally transferred to 60 mm diameter × 15 mm tissue culture dishes containing the same medium. The dishes are maintained at 37° C. in a humidified atmosphere of 5% $CO_2$ in air. Medium is changed after 12, 36, 60 and 84 hrs., and subsequently twice weekly.

Figure 13:
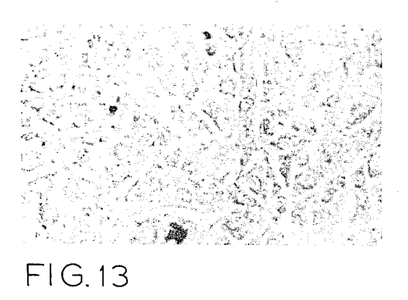
FIG. 13 shows a formalin (10%) fixed monolayer of epitheloid endocrine cells derived under culture from mildly digested human neonate pancreatic tissue (X 650)
Figure 14:
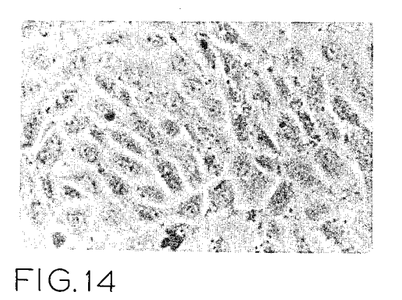
FIG. 14 shows a monolayer of non-granulated epitheloid cells which appear in the culture after deterioration of the cells of FIG. 13 (X 650)
Figure 15:
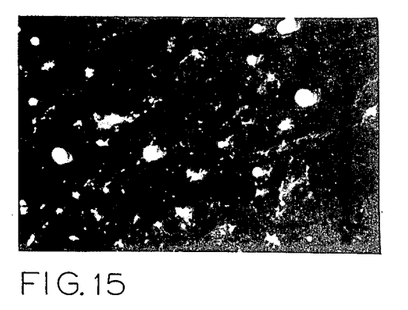
FIG. 15 shows ILS's obtained from continued culture of the cells of FIG. 16, under dissecting microscopy against a black background (X 40)
Figure 16:
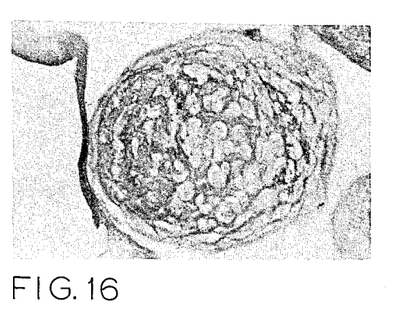
FIG. 16 shows a section of an ILS stained with Gomori's aldehyde fuchsin (X 1290).

Examination of the dishes by phase contrast microscopy at the time of plating reveals numerous cell clusters of varying size. They appear to be endocrine cells since morphologically indentifiable acinar cells are completely absent. Forty-eight hours after plating, about half the cell clusters become attached to the bottoms of the culture dishes and become flattened, forming monolayer sheets. The unattached clusters are transferred to new dishes, where they become attached within the next 48 hours. The monolayers are epitheloid, consisting of granulated, polygonal cells with large vesicular nuclei as shown in FIG. 13. By 2 weeks, the monolayers begin to deteriorate and are replaced by a new cell type. These cells are also epitheloid, but are quite distinct, having had no visible granules as shown in FIG. 16. Within 2 days of the first occurrence of the second type of epithelial cells, fibroblastoid cells make an appearance. This results in epithelial monolayers being surrounded and covered by a layer of loosely arranged fibroblasts. Within another 5-8 days large numbers (300-500) of multicellular structures (ILS's) appear throughout the petri dishes attached to the underlying stromatic layer as shown in FIG. 15. Under the dissecting stereomicro-scope, the structures are spherical/oval, opaque, milky white bodies 50-300 μm in diameter, morphologically similar to freshly isolated pancreatic islets of Langerhans. These ISL's can be easily detached by the gentle streaming of medium around them. Pancreatic pieces treated with collagenase/trypsin behaved identically to those treated with collagenase/hyaluronidase. Use of the former digestion method, however, yields fewer numbers of the initial epitheloid clusters and ultimately a reduced yield of ILS's.

Transfer of few (5-10) ILS's to a new dish initiates the complete cycle described above, so that large numbers of ILS's are formed within 3-4 weeks. The ILS's can be harvested for use or for subculturing to yield further generations of ILS's.

The insulin content, insulin secretion and the biosynthesis of proinsulin-insulin and other islet proteins ([$^3$H] leucine incorporation) were determined for the ILS's thereby obtained using the same methods as described above. The incubation conditions used in one series of experiments, however, were modified as follows. After a preliminary (45 min.) incubation in KRB, ILS's were subjected to an intermediate incubation in the presence of freshly prepared 3 mM alloxan (5 min.), 2.5 mM azaserine (30 min.), or 2 mM streptozotocin (30 min.). Whereas alloxan and azaserine solutions were made directly in KRB, streptozotocin was first dissolved in 1 mM citrate buffer (pH 4.2), containing 0.9% sodium chloride. A 10 μl aloquot of the stock solution was then added to KRB to give the desired concentration. Following the intermediate incubation, ILS's were washed 3 times with KRB and finally incubated for 2 hr. in buffer containing 20 mM glucose and 100 μCi/ml of L-[4,5-$^3$H] leucine (40 Ci/mmole) (New England Nuclear Corporation, Boston, Mass).

INSULIN CONTENT

The insulin content of the ILS's obtained from culturing of the cell clusters was determined at the time of subculture. At the time of the first transfer, the immunoreactive insulin content was 180-220μ units/ILS. At the time of subsequent transfers insulin content was more variable, ranging from 60-180μ units/ILS.

INSULIN RELEASE

The insulin release was determined in experiments performed at the time of the second transfer. During 90 min. batch-type incubations in KRB, hormone release was 3-5μ Units/ILS. The secretion rate was unresponsive to high glucose (20 mM), even in the presence of theophylline (10 mM).

PROTEIN BIOSYNTHESIS

Protein biosynthesis was determined in experiments performed at the time of the second transfer. The rates of [$^3$H] leucine incorporation are given in Table 2. The ILS's incorporated label into both proinsulin-insulin as well as non-insulin proteins, although synthesis was not responsive to glucose. About ⅓ to ½ of the counts incorporated into TCA precipitable protein from acid alcohol extracts were also immunoprecipitable. Proinsulin-insulin thus accounts for 15-19% of total protein synthesized. Protein biosynthesis was not affected by exposure of ILS's to azaserine. Streptozotocin and alloxan, however, inhibited synthesis by almost 50%. The citrate buffer used for incubation during exposure to streptozotocin was not responsible for the inhibitory effect.

HISTOLOGICAL CHARACTERIZATION

Histological studies indicate that the ILS's were oval in shape, and were composed of polyhedral cells containing distinct nuclei. Sections stained by Gomori's chromium haematoxylin phloxine method revealed a patchy distribution of blue staining cells of varying intensity. In some ILS's the blue staining cells were found to occupy a central position. Sections stained by aldehyde fuchsin showed a similar distribution of purple cells.

TABLE 2

| | Protein Biosynthesis ([$^3$H] leucine incorporation) by culture-derived islet-like structures | | | |
|---|---|---|---|---|
| | cpm/2 h/ILS[a] | | | |
| | Acid alcohol extractable proteins[b] | | TCA precipitable proteins not extractable by acid alcohol | Biosynthesis of Proinsulin + Insulin as % of total protein |
| Glucose (mM) | Proinsulin + Insulin[c] | TCA precipitable proteins[d] | | |
| 0 | 3362 ± 343 | 9423 ± 1080 | 12969 ± 1013 | 15.0 |
| 2 | 5156 ± 559 | 11577 ± 922 | 18103 ± 963 | 17.4 |
| 20 | 5264 ± 499 | 9833 ± 1170 | 18158 ± 842 | 18.8 |

Notes:
[a]Results are given as means ± S.E.M., n = 4.
[b]ILS's were extracted in 1 ml of acid alcohol (67 ml ethanol, 31 ml water, 2 ml 12N HCl)
[c]Radioactive proinsulin and insulin was determined by the double antibody precipitation method of Zucker and Logothetopoulos described above.
[d]Biosynthesis of proteins in both the acid alcohol extract of the ILS's and proteins remaining in ILS's which were not extracted by acid alcohol was determined by measuring [$^3$H] leucine incorporation into trichloroacetic acid (TCA) precipitable protein.

The histological staining reactions, as well as the functional assays, namely the insulin biosynethesis and secretion indicate that the ILS's contain functioning beta cells. This is further supported by the differential sensitivity of ILS's to alloxan and streptozotocin, as opposed to azaserine. It is known that alloxan and streptozotocin are cytotoxic compounds, specific for the pancreatic beta cells. We have found that 2.5 mM azaserine inhibited protein syntheis by freshly isolated rat pancreatic acinar cells by 80%, whereas the islets are unaffected. In the present investigation, protein synthesis by the ILS's was found to be inhibited by alloxan and streptozotocin but not by azaserine.

The ILS's appear to be functionally immature, as evidenced by their failure to respond to glucose challenge with increased insulin biosyntheis or secretion. In this regard, they are similar to the human fetal pancreas in vivo or human fetal pancreatic fragments maintained in culture, as well as islets maintained in culture obtained from an adult human. Human fetal islets, as well as fetal islets of monkey, rat and rabbit are also known to fail to respond to glucose.

We claim:

1. A method for producing mammalian pancreatic islet-like structures hereinafter called ILS's, having histological characteristics and insulin-producing properties corresponding to those of natural isolated fetal pancreatic islets and islets obtained from adult animals maintained in culture, comprising establishing under conditions promoting the growth of mammalian cells, a culture comprising at least one pancreatic tissue-derived body attached to a substrate compatible with mammalian cells and capable of accepting the attachment of mammalian pancreatic islet tissue thereto, and immersed in a liquid tissue culture medium capable of sustaining mammalian cell growth, said body being selected from the group consisting of:
   (a) intact mammalian pancreatic islets isolated directly from postpartal pancreatic tissue and present in the culture at an islet population density of less than about 10 islets per ml of the liquid culture medium;
   (b) pieces of mammalian postpartal pancreatic duct;
   (c) clusters of coherent pancreatic cells obtained by mild digestion of pieces of whole mammalian postpartal pancreas with a solution of a connective tissue-lysing enzyme, said clusters being substantially free of pancreatic exocrine tissue;
   (d) cells characterized by having an oblong flat configuration with highly serrated ends and tenacious attachment to the substrate and obtained by culturing a body selected from the group consisting of said bodies (a), (b), and (c) above and (e) below for prolonged periods in said culture under said mammalian cell-growth promoting conditions;
   (e) ILS's obtained by culturing a body selected from the group consisting of said bodies (a), (b), (c), and (d) for prolonged periods under said mammalian cell-growth promoting conditions; and maintaining said culture for a period sufficient to permit neogenesis of discrete ILS's connected to cell tissue outgrowing from the body and attached to the substrate; detaching said ILS's from the said outgrowing tissue; and recovering said detached ILS's from the culture.

2. Method as claimed in claim 1 wherein said at least one body comprises a piece of mammalian pancreatic duct.

3. A method as claimed in claim 2 wherein said duct piece has a maximum dimension of from about 0.5 to about 5 mm.

4. Method as claimed in claim 3 wherein said maximum dimension is about 0.5 mm to about 2 mm.

5. Method as claimed in claim 1 wherein said at least one body comprises a plurality of mammalian pancreatic duct pieces.

6. A method as claimed in claim 5 wherein said pieces are maintained on the substrate at a spacing sufficient to avoid overlapping of tissues outgrowing from adjacent pieces.

7. Method as claimed in claim 5 wherein said pieces are maintained on the substrate at a spacing of at least about 5 mm.

8. Method as claimed in claim 7 wherein said spacing is at least about 10 mm.

9. Method as claimed in claim 5 comprising initially seeding a plurality of said duct pieces into a culture vessel providing said substrate and containing said culture medium, and removing from the culture vessel any duct pieces that remain unattached to the substrate after culturing for a period of about 2 weeks.

10. Method as claimed in claim 9 including the step of removing from the culture vessel any detached duct pieces that float in the medium after a period of about 4 weeks from the data of initial seeding.

11. Method as claimed in claim 2 comprising maintaining the culture for a period of at least about 2 weeks.

12. Method as claimed in claim 11 wherein the liquid culture medium is changed at intervals of about 1 to 7 days throughout the period of culturing.

13. Method as claimed in claim 1 wherein said at least one body comprises an isolated intact mammalian pancreatic islet.

14. Method as claimed in claim 1 wherein said at least one body comprises a plurality of isolated intact mammalian pancreatic islets.

15. Method as claimed in claim 14 wherein said islets are maintained on the substrate at a density of less than about 5 islets per ml of culture medium.

16. Method as claimed in claim 15 wherein said density is about 1 to 3 islets per ml of culture medium.

17. Method as claimed in claim 14 comprising initially seeding said islets in a culture vessel, providing said substrate, and containing said culture medium, at a density in excess of 10 inlets per ml of culture medium, and removing any detached islets from the culture vessel at intervals during the first 10 weeks of culturing.

18. Method as claimed in claim 13 comprising maintaining the culture for a period of at least about 8 weeks.

19. Method as claimed in claim 18 including changing the liquid culture medium initially at intervals of about 12 to 24 hours for a period of about 3 to 4 days from the data of seeding and subsequently at intervals of about 5 to 10 days.

20. Method as claimed in claim 14 wherein said islets are obtained by digestion of pieces of whole pancreatic tissue under mild digestion conditions with a solution of a connective tissue-lysing enzyme for a period sufficient to liberate the islets from the tissue.

21. Method as clamied in claim 20 wherein said pieces are contacted with said enzyme solution for the minimum period of time required to liberate the islets.

22. Method as claimed in claim 20 wherein digestion is conducted under such mild conditions that the liberated islets have vestiges of pancreatic ductules discernible at their peripheries.

23. Method as claimed in claim 1 wherein said at least one body comprises a culster of pancreatic cells obtained by mild digestion of pieces of whole mammalian pancreas with a solution of connective tissue-lysing enzyme.

24. Method as claimed in claim 23 wherein said pieces have a maximum dimension of about 0.5 to about 5 mm.

25. Method as claimed in claim 24 wherein said maximum dimension is about 0.5 to about 2 mm.

26. Method is claimed in claim 20 or 23 wherein said enzyme solution has a tissue-lysing potency no greater than that of a reference solution containing about 1,500 Units of collagenase per ml.

27. Method as claimed in claim 20 or 23 wherein said enzyme solution has a tissue-lysing potency no greater than that of a reference solution containing about 1,000 Units of collagenase per ml.

28. Method as claimed in claim 20 or 23 wherein said enzyme solution has a tissue lysing potency no greater than that of a reference solution containing about 750 Units of collagenase per ml.

29. Method as claimed in claim 20 or 23 wherein said mild digestion is such that the degree of tissue lysis corresponds approximately to that obtained from digestion with a collagenase solution containing about 750 collagenase Units per ml for about 12 to 15 minutes at about 37° C.

30. Method as claimed in claim 20 or 23 wherein said enzyme solution contains a mixture of collagenase and hyaluronidase.

31. Method as claimed in claim 1 wherein said at least one body comprises a plurality of said clusters as defined in paragraph (c) thereof.

32. Method as claimed in claim 31 wherein said clusters are seeded in a culture vessel providing said substrate and containing said culture medium at a spacing that avoids overlapping on the substrate of epitheloid monolayers that form from the clusters.

33. Method as claimed in claim 23 wherein said culture is maintained for a period of at least about 25 days.

34. Method as claimed in claim 33 including changing the liquid culture medium initially at intervals of about 12 to 24 hours for the first 3 to 4 days from the data of seeding and subsequently at intervals of about 5 to 10 days.

35. Method as claimed in claim 1 wherein said liquid culture medium contains glucose at a molar concentration of about 5 to 20 mM.

36. Method as claimed in claim 32 wherein said glucose concentration is about 10 mM.

37. Method as claimed in claim 1 wherein said medium is maintained equilibrated with a 5% $CO_2$/air mixture.

38. Method as claimed in claim 1 wherein said medium is maintained under a water-saturated atmosphere.

39. Method as claimed in claim 1 wherein said culture medium contains mammalian serum.

40. Method as claimed in claim 39 wherein the content of mammalian serum is about 5 to 20% by volume based on the volume of the mixture.

41. Method as claimed in claim 39 wherein the serum is heterologous with respect to said body.

42. Method as claimed in claim 39 or 40 wherein said serum is fetal calf serum.

43. Method as claimed in claim 39 wherein the medium contains in admixture about 15% by volume fetal calf serum based on the volume of the mixture.

44. Method as claimed in claim 1 wherein the culture medium is maintained at a temperature of 35° to 40° C.

45. Method as claimed in claim 44 wherein said temperature is about 37° C.

46. Method as claimed in claim 1 wherein the culture medium contains at least one antibiotic present in an effective microorganism growth-inhibitive concentration.

47. Method as claimed in claim 46 wherein the medium contains about 50 to about 200 μU/ml penicillin and about 50 to about 100 μg/ml streptomycin.

48. Method as claimed in claim 47 wherein the medium contains about 100 μU/ml penicillin and about 100 μg/ml streptomycin.

49. A method for producing mammalian pancreatic islet-like structures hereinafter called ILS's, having histological characteristics and insulin-producing properties similar to those of natural isolated fetal pancreatic islets and islets obtained from adult animals maintained in culture, comprising sub-culturing neogenetic ILS's harvested from a culture of pancreatic tissue-derived bodies, and harvesting neogenetic ILS's from the sub-culture.

50. A method as claimed in claim 49 wherein the sub-culturing comprises establishing under conditions promoting the growth of mammalian cells, a culture comprising the first-mentioned neogenetic ILS's attached to a substrate compatible with mammalian cells and capable of accepting the attachment of pancreatic islet tissue thereto, and immersed in a liquid tissue culture medium capable of sustaining mammalian cell growth, and maintaining the culture for a period sufficient to permit neogenesis of discrete ILS's connected to cell tissue outgrowing from said first-mentioned neogenetic ILS's.

* * * * *